(12) United States Patent
Tranzeat et al.

(10) Patent No.: US 10,709,804 B2
(45) Date of Patent: Jul. 14, 2020

(54) MALODOR COUNTERACTING COMPOSITIONS AND METHOD FOR THEIR USE

(71) Applicant: FIRMENICH SA, Satigny (CH)

(72) Inventors: Lyse Tranzeat, West Drayton (GB); Nicholas O'Leary, Pennington, NJ (US); Wessel-Jan Kos, Beaconsfield (GB)

(73) Assignee: Firmenich SA, Satigny (CH)

(*) Notice: Subject to any disclaimer, the term of this patent is extended or adjusted under 35 U.S.C. 154(b) by 194 days.

(21) Appl. No.: 15/474,764

(22) Filed: Mar. 30, 2017

(65) Prior Publication Data
US 2017/0266334 A1 Sep. 21, 2017

Related U.S. Application Data

(60) Continuation of application No. 13/774,288, filed on Feb. 22, 2013, now abandoned, which is a division of application No. 12/438,713, filed as application No. PCT/IB2007/053399 on Aug. 24, 2007, now abandoned.

(30) Foreign Application Priority Data

Aug. 28, 2006 (EP) .................................. 06119640

(51) Int. Cl.
| | |
|---|---|
| *A61L 9/013* | (2006.01) |
| *A01K 1/015* | (2006.01) |
| *A61K 8/02* | (2006.01) |
| *A61K 8/33* | (2006.01) |
| *A61K 8/35* | (2006.01) |
| *A61K 8/37* | (2006.01) |
| *A61K 8/40* | (2006.01) |
| *A61K 8/49* | (2006.01) |
| *A61L 9/01* | (2006.01) |
| *A61Q 5/00* | (2006.01) |
| *A61Q 5/02* | (2006.01) |
| *A61Q 5/12* | (2006.01) |
| *A61Q 13/00* | (2006.01) |
| *A61Q 15/00* | (2006.01) |
| *A61Q 19/00* | (2006.01) |
| *A61Q 19/10* | (2006.01) |
| *C07D 307/33* | (2006.01) |
| *C07D 315/00* | (2006.01) |
| *C09B 67/40* | (2006.01) |
| *C11D 3/50* | (2006.01) |
| *D06M 13/00* | (2006.01) |
| *C11B 9/00* | (2006.01) |
| *C11D 3/00* | (2006.01) |

(52) U.S. Cl.
CPC ............ *A61L 9/013* (2013.01); *A01K 1/0152* (2013.01); *A61K 8/0208* (2013.01); *A61K 8/33* (2013.01); *A61K 8/35* (2013.01); *A61K 8/37* (2013.01); *A61K 8/40* (2013.01); *A61K 8/4973* (2013.01); *A61L 9/01* (2013.01); *A61Q 5/00* (2013.01); *A61Q 5/02* (2013.01); *A61Q 5/12* (2013.01); *A61Q 13/00* (2013.01); *A61Q 15/00* (2013.01); *A61Q 19/002* (2013.01); *A61Q 19/10* (2013.01); *C07D 307/33* (2013.01); *C07D 315/00* (2013.01); *C09B 67/0082* (2013.01); *C11B 9/003* (2013.01); *C11B 9/0023* (2013.01); *C11B 9/0034* (2013.01); *C11D 3/0068* (2013.01); *C11D 3/50* (2013.01); *D06M 13/005* (2013.01)

(58) Field of Classification Search
CPC .......... A61L 9/013; A61L 9/01; C11B 9/0023; C11B 9/003; C11B 9/0034; C11D 3/0068; C11D 3/50; A01K 1/0152; A61K 8/0208; A61K 8/33; A61K 8/35; A61K 8/37; A61K 8/40; A61K 8/4973; A61Q 5/00; A61Q 5/02; A61Q 5/12; A61Q 13/00; A61Q 15/00; A61Q 19/002; A61Q 19/10; C07D 307/33; C07D 315/00; C09B 67/0082; D06M 13/005

See application file for complete search history.

(56) References Cited

U.S. PATENT DOCUMENTS

| | | | | |
|---|---|---|---|---|
| 6,177,400 B1* | 1/2001 | Mimoun | ............. | C07C 31/1355 512/22 |
| 2003/0199412 A1* | 10/2003 | Gupta | .................... | C11D 3/124 510/285 |

FOREIGN PATENT DOCUMENTS

WO   WO-2006095200 A1 * 9/2006 ............... A61K 8/11

* cited by examiner

*Primary Examiner* — John Pak
*Assistant Examiner* — Andriae M Holt
(74) *Attorney, Agent, or Firm* — Armstrong Teasdale LLP

(57) ABSTRACT

The invention relates to a malodor counteractancy or counteracting (MOC) method that resorts to the use of specific malodor counteracting (MOC) mixtures of fragrance ingredients. More particularly, the invention relates to new MOC compositions capable of neutralizing or masking in an efficient manner malodors of a large variety of such as body or as malodors, kitchen malodors, toilet and bathroom malodors, and tobacco malodor. The novel MOC compositions of the invention contain at least one nitrile material in combination with another fragrance material and can be used in any finished consumer products such as air fresheners, kitchen or toilet/bathroom cleaning or freshening products, textile treatment products and products for application on the human skin or hair, or on animal fur, litter containers or cages.

13 Claims, 12 Drawing Sheets

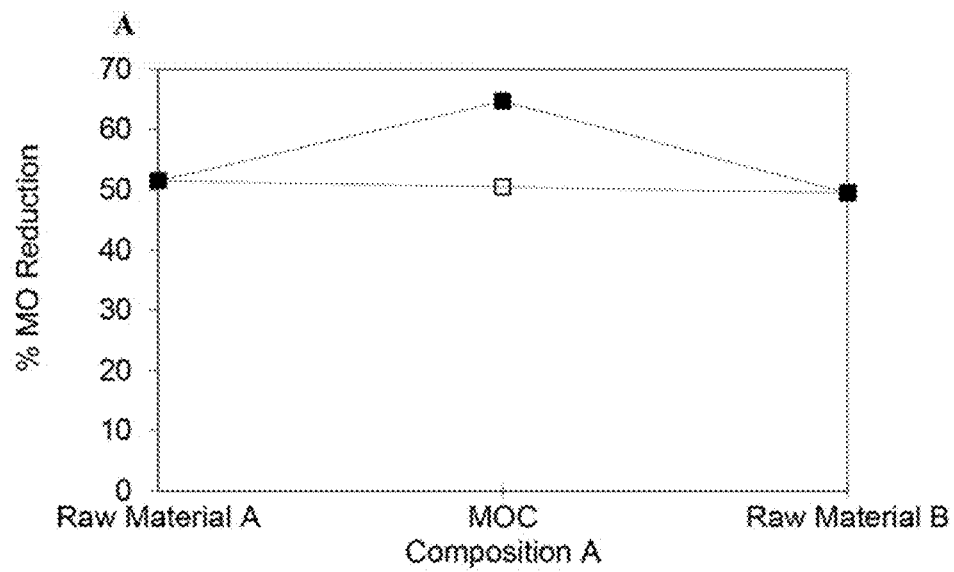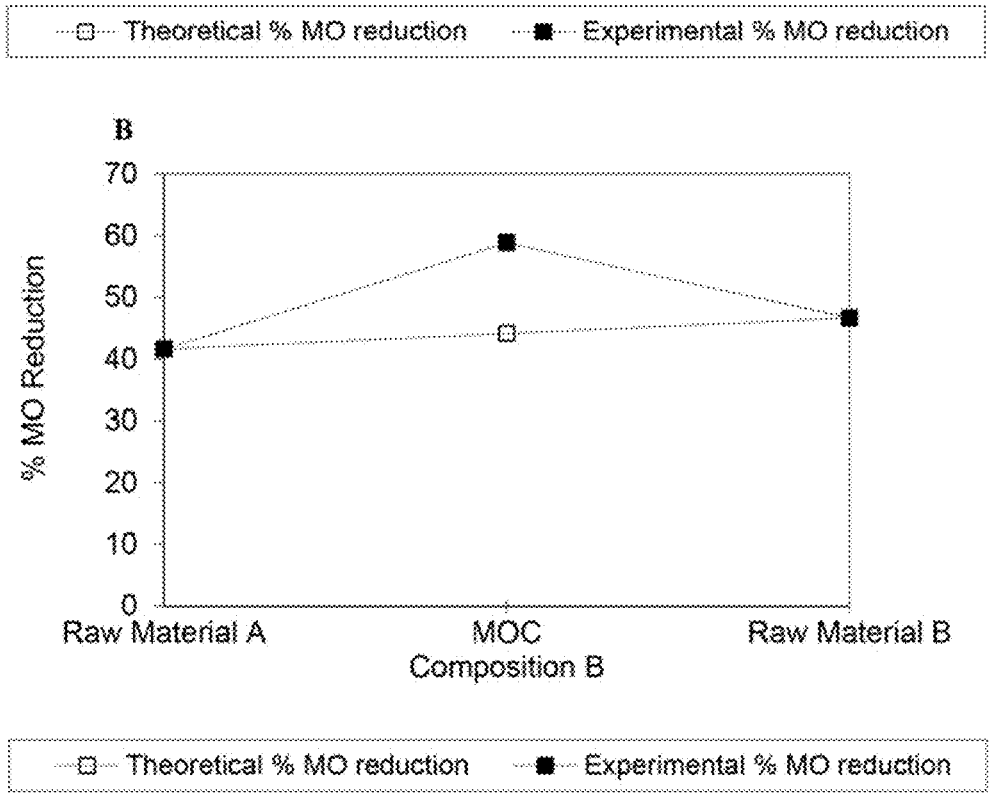
Fig. 1

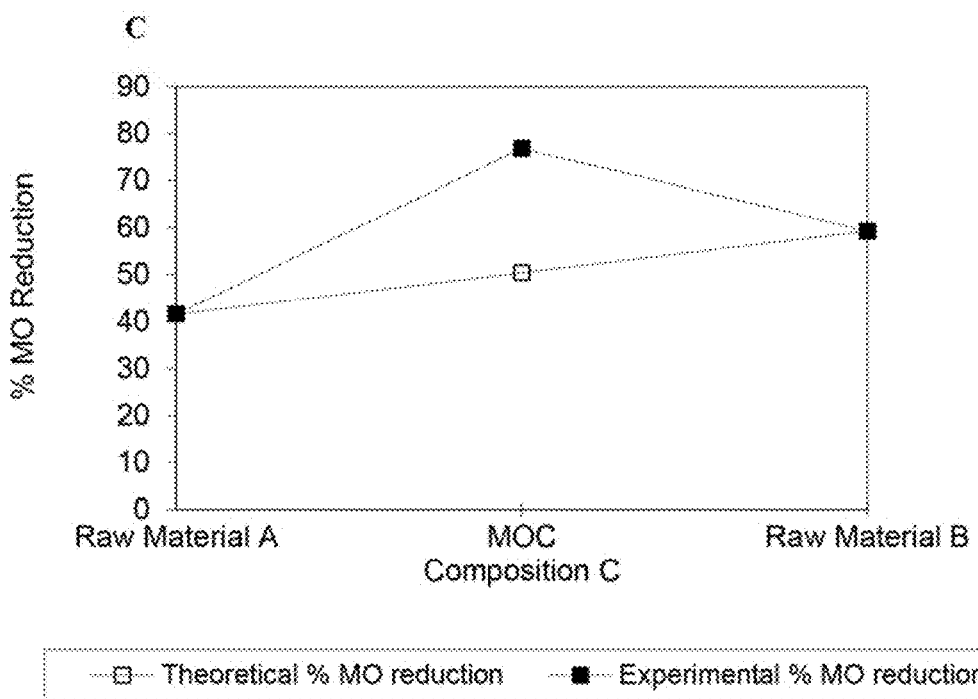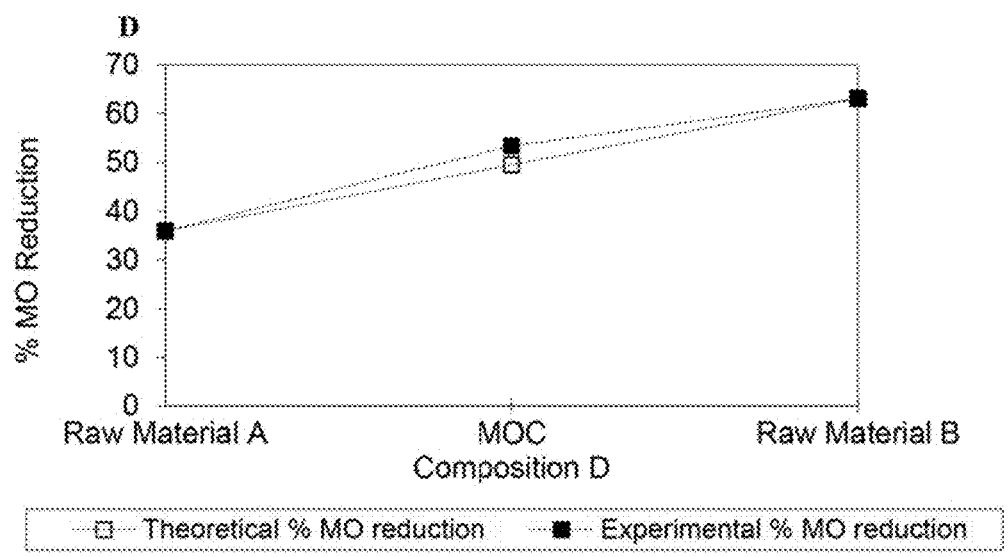
Fig. 1

Fig. 2
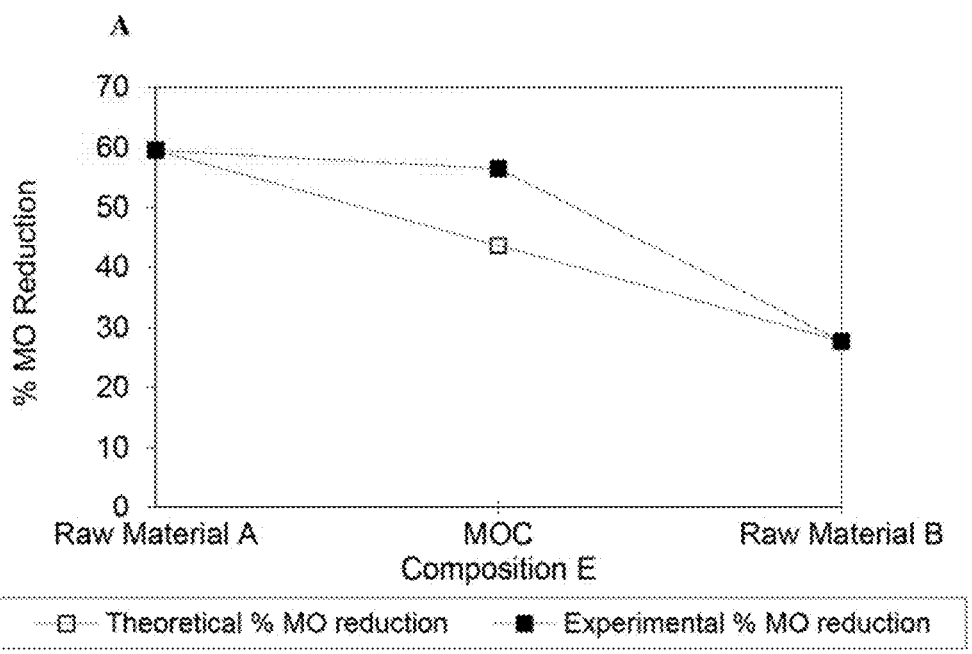
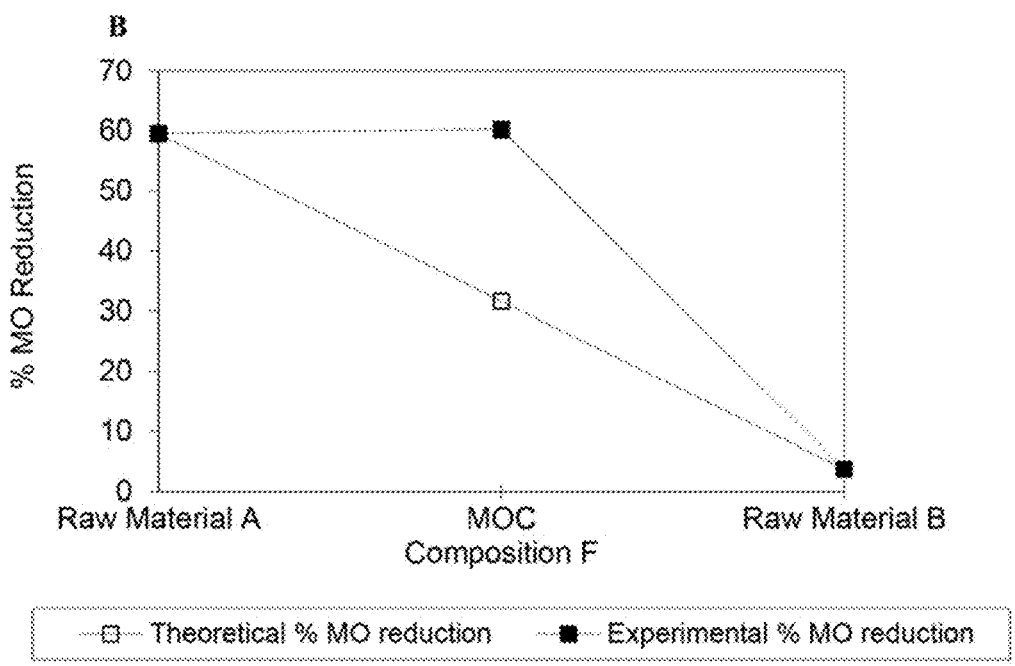

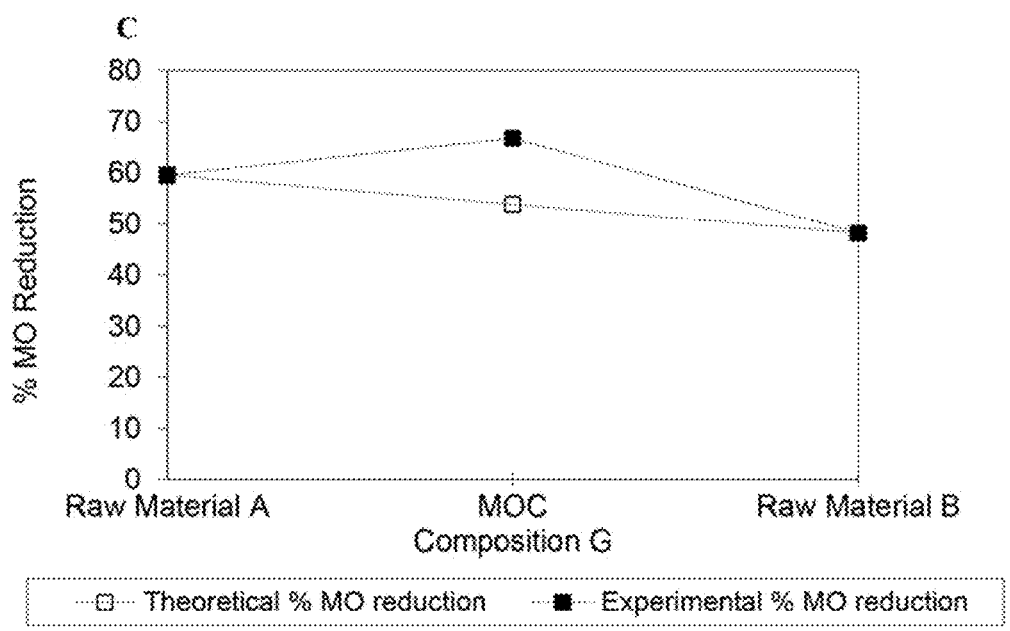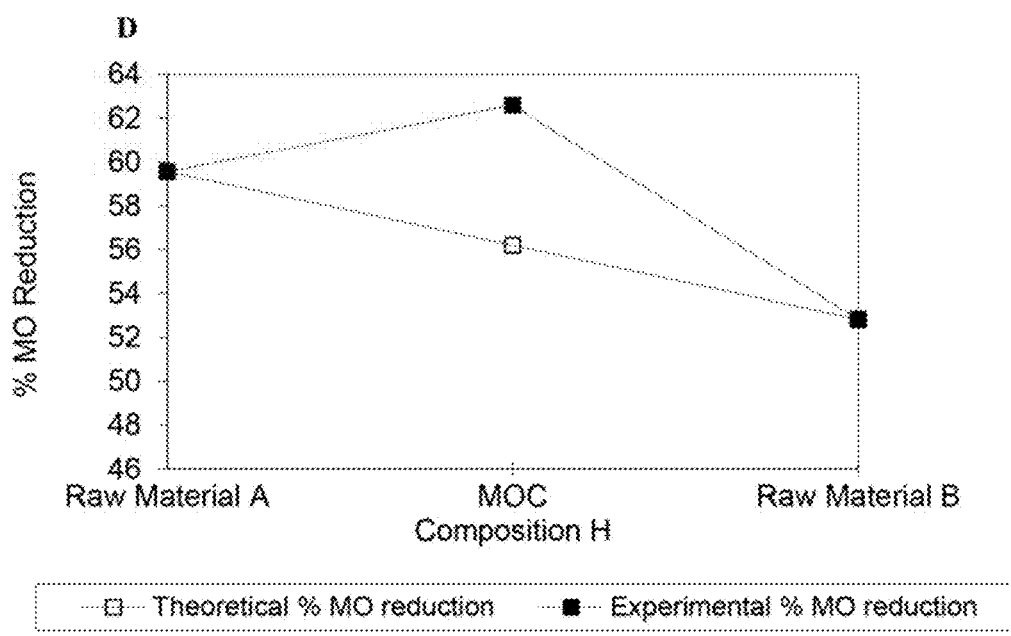

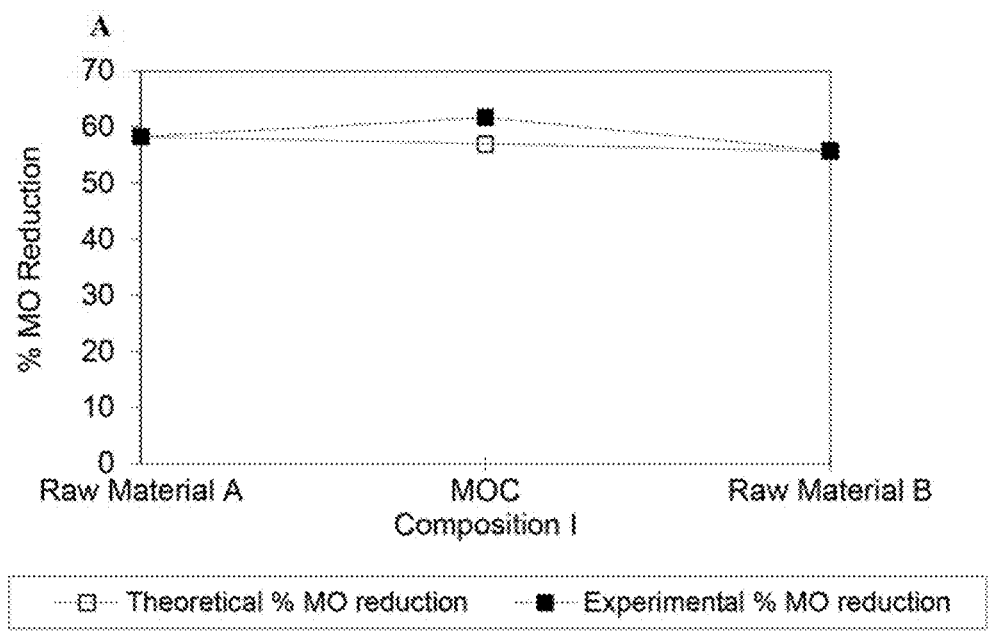
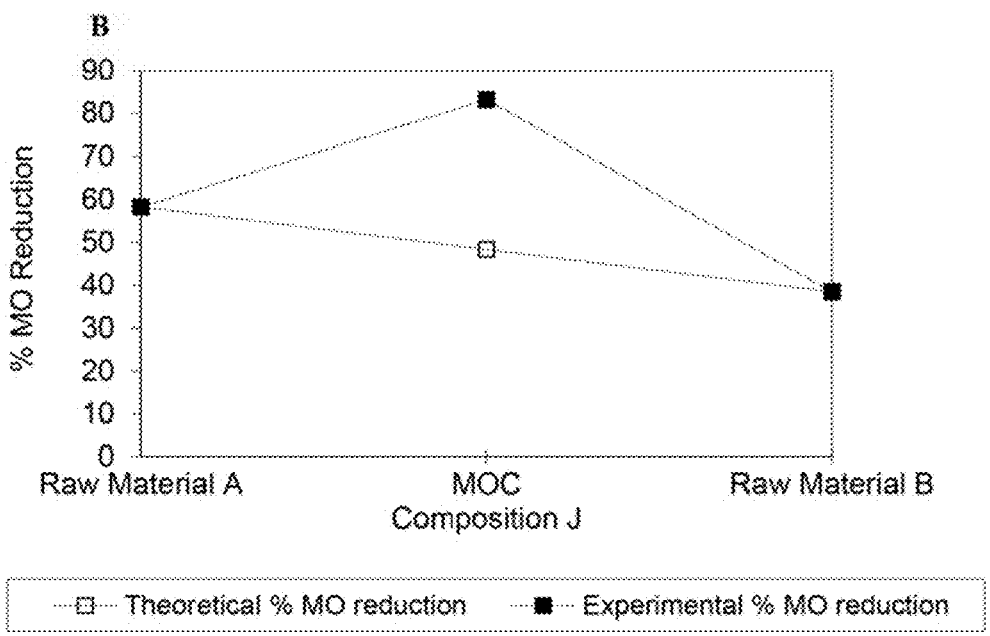

MALODOR COUNTERACTING COMPOSITIONS AND METHOD FOR THEIR USE

CROSS REFERENCE TO RELATED APPLICATIONS

This application is a continuation of U.S. patent application Ser. No. 13/744,288, filed on Feb. 22, 2013, which is a division of U.S. patent application Ser. No. 12/438,713, filed on Aug. 25, 2009, which is a National Stage Entry International Patent Application Serial No. PCT/IB07/53399, claiming priority to European Patent Application Serial No. 06119640.8, filed on Aug. 28, 2006, the entire contents of which are hereby incorporated by reference in their entirety.

TECHNICAL FIELD

The present invention relates to a malodor counteractancy or counteracting (MOC) method that resorts to the use of specific malodor counteracting (MOC) mixtures of fragrance ingredients. More particularly, the invention relates to new MOC ingredients capable of neutralizing or masking in an efficient manner malodors of a large variety of origins and which can be encountered in the air, on textiles, bathroom or kitchen surfaces, etc. The novel MOC compositions of the invention contain at least one material of group (I) and at least one material of group (II), as defined below.

The invention also relates to methods of use of the MOC compositions and ingredients to counteract malodor and of any finished consumer products containing them, such as air fresheners, kitchen or toilet/bathroom cleaning or freshening products, textile treatment products and products for application on the human skin or hair, or on animal fur and skin, litter containers and cages.

PRIOR ART

The prior art richness in reports of methods to counteract and/or mask malodors is such that a complete review of all the methods and compositions prior reported in this context is impossible here. It is clear however that there still exists a need to continue searching alternative ways of solving the malodor problem, as evidenced by the constant publications in this field.

Early work by A. A. Schleppnik, described in a series of US patents, namely U.S. Pat. Nos. 4,187,251, 4,310,512 and 4,622,221 and 4,719,105, disclosed the use of a variety of cyclopentyl, cyclohexyl and phenyl derivatives having a lateral chain typically comprising a carboxylic functional group, mostly aldehydes, ketones and more particularly ester derivatives of the indicated cyclic moiety.

Also, an early review on malodor control, situating the objectives of research in this field, the general chemical solution approaches possible and the potential applications thereof, was presented by H. Hoffmann in Perfumer & Flavorist, 1986, 11, pages 1 to 7.

In more recent work published in U.S. Pat. No. 5,795,566, to D. Joulain, there were proposed deodorant compositions containing at least two aldehydes, selected from specifically defined groups.

Useful reference can also be made to the mixtures disclosed in EP 780132-A1, to International Flavors & Fragrances, formed of musky, citrus and minty type fragrance ingredients, and more particularly to mixtures of Galaxolide with mint oil and citrus terpenes. In a more recent publication, US 2004/0156742, inventors from this same company proposed mixtures of specific esters to counter air malodor.

C. E. Kaiser et al., in WO 00/55288, proposed a method of masking amine type malodors via addition of materials capable of forming Schiff type bases with the amines generating the malodor, whereas J. Costa et al., from the same company, have recently postulated in US 2004/0034789 that malodor coverage and/or masking should be essentially based on the principle that the materials used for this purpose must have a high air diffusion coefficient. The inventors in this latter publication proposed mixtures of compounds comprising phenyl and $C_5$ ring moieties and having well defined air diffusion coefficients. In spite of the other prior known disclosures of phenyl and cyclopentyl derivatives taught for the same purpose, the malodor masking mixtures specifically disclosed in this latter document are shown to counteract a variety of malodors of different origins, and one can find in this document a useful description of the typical malodor compositions that are used generally for testing efficiency of malodor coverage and/or masking.

W. Neugebauer et al., in International patent publication WO 03/070871, addressed the problem of covering the malodor generated during soaking and hand washing of laundry and postulated the use of one or more specific fragrance ingredients. Although one can find amongst the proposed ingredients a suggestion to combine chemicals such as damascone and decenyl nitrile with a third component of more complex structure, there is no suggestion that the simple combination of materials as are presently taught here would efficiently provide a MOC effect.

Still amongst the more recent patent literature in this field, one can cite the report of Thomas McGee et al., in U.S. Pat. No. 6,610,648, for example, related to the use of low odor intensity compounds to cover offensive odors encountered in the air and a large variety of surfaces. Column 1 of this document, in particular lines 10 to 50, expose in a general manner the background of this technical field and the problem that the skilled practitioner is confronted with, and its disclosure is included herein by reference to help situate the technical field of relevance to the present invention. This document also summarizes succinctly the types of approaches that have been used in prior solution-providing disclosures in this field and proposes a solution based on particular compounds that are said to act synergetically, whilst being individually odorless or of a neutral odor.

The description above clearly shows that, although many attempts have been made at solving malodor masking or coverage, or the development of malodors in air or in a variety of surfaces, there is a constant need for MOC compositions and methods for their use. The present invention provides an original and advantageous contribution to the solution of this problem.

DESCRIPTION OF THE INVENTION

We have now surprisingly established that mixtures of the compounds of groups (I) and (II) described below possess very useful MOC properties and that they are capable of masking and/or neutralizing a large variety of malodors of importance in the design and conception of fragrance compositions and consumer products intended for efficient prevention and/or masking of malodor development in the human or animal bodies, or generated as a result of human and animal general activities.

The present invention relates to MOC compositions comprising at least one ingredient selected from Group (I)

compounds and at least one ingredient selected from Group (II) compounds, wherein the Group (I) compounds and the Group (II) compounds are defined as follows:

A. Group (I):
(i) Compounds of formula

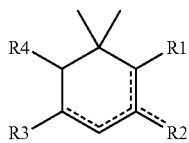

having one or two double bonds in the $C_6$ ring, located in the positions indicated by the dotted lines and wherein:
a) $R^1$ represents a group of formula

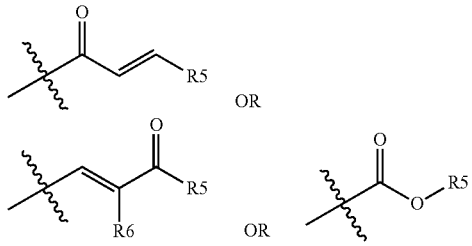

$R^5$ being hydrogen or a $C_1$ to $C_4$ linear or branched alkyl radical, or an allyl radical, and $R^6$ representing hydrogen or a $C_1$ to $C_4$ linear or branched alkyl radical;
b) $R^2$ is H, $=CH_2$ or $-CH_3$;
c) $R^3$ is H or a $C_1$ to $C_4$ linear or branched alkyl radical; and
d) $R^4$ is H or a $C_1$ to $C_4$ linear or branched alkyl radical;
the sum of carbons atoms in groups $R^2$, $R^3$ and $R^4$ being less than, or equal to, 7;
or
(ii) Compounds of formula

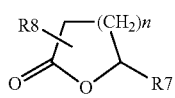

in which n is 1 or 2, $R^7$ represents a $C_1$ to $C_{10}$ linear or branched alkyl or allyl radical, and $R^8$ is H or a $C_1$ to $C_4$ linear or branched alkyl radical;
or
(iii) A compound selected from group consisting of the compounds of formulae

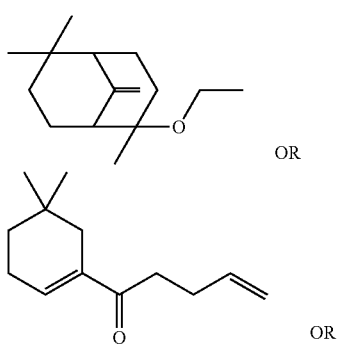

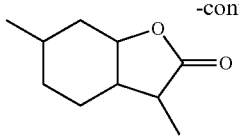

B. Group (II)—Nitriles.
Specific examples of suitable compounds of formula (I) are represented by the following structures:

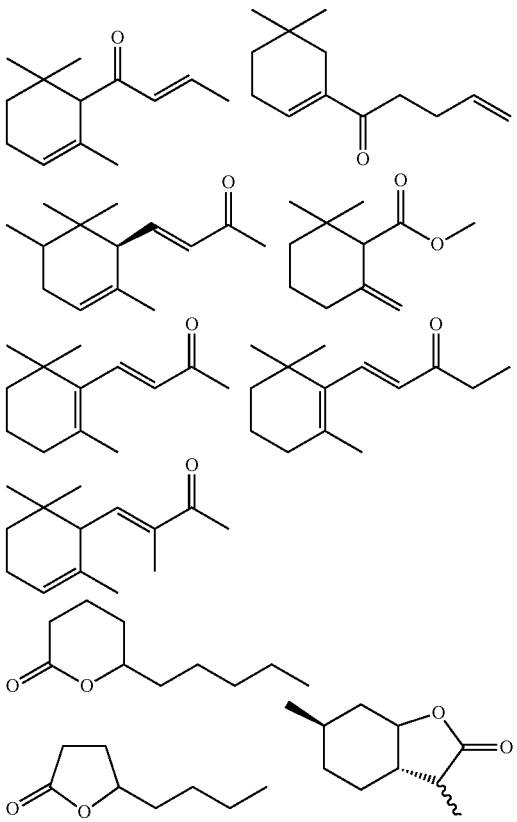

all of these materials being fragrance ingredients available from Firmenich SA, Geneva, Switzerland.

Following a preferred embodiment of the invention, the at least one compound from Group (I) is a compound of formula (I) comprising a single double bond in the ring, said double bond being located in a position alpha relative to the substituting side chain of the ring carrying the functional group $R^1$.

Following another preferred embodiment, the at least one compound from Group (I) is selected from the group consisting of α-methyl-ionone, undecalactone, (+−)-methyl-2,2-dimethyl-6-methylene-1-cyclohexanecarboxylate, (E)-4-(2,6,6-trimethyl-2-cyclohexen-1-yl)-3-buten-2-one) and α-damascone.

In an even more preferred embodiment, the at least one compound from Group (I) is selected from α-methyl-ionone and α-damascone.

Preferred nitriles from Group (II) are selected from the group consisting of cinnamonitrile or 3-phenyl-2-propenenitrile, citronitrile, geranyl nitrile, cytronellyl nitrile, 2-propyl-1-heptanenitrile, dodecanenitrile, all of these materials being ingredients available from Firmenich SA, and the nitrile described in U.S. Pat. No. 6,180,814, or 3-(2,3-dimethyl-2 (3)-cyclopenten-1-yl)butanenitrile and 3-(2-methyl-3-methylene-1-cyclopentyl)butanenitrile.

In an even more preferred embodiment, the at least one nitrile of Group (II) is selected from citronellyl nitrile, 2-propyl-1-heptanenitrile and the nitrile described in U.S. Pat. No. 6,180,814.

As will become apparent from the examples presented further on, we have been able to establish that the combinations of one compound from Group (I) with one compound from Group (II) provide a synergetic MOC effect as compared to the MOC effect obtained by the use of either compound alone, or as compared to the theoretical MOC effect that would have been expected from the simple addition of the individual MOC contributions of these two materials when present in a wide range of relative proportions in a mixture. These combinations can be employed advantageously for counteracting malodor of a variety of origins, such as sweat and other body malodors, kitchen (cooking) and toilet (urine, faeces) malodors, gasoline, amine and sulfur type odors, the odor of tobacco smoke, animal litter malodors, etc.

By a "synergetic" effect it is understood here an effect which is not the simple sum or addition of the MOC effect expected when the two materials would have been admixed in a 50:50 proportion in the mixture, or in any other relative proportion. The contribution from each material, as a function of its concentration relative to the weight of the selected testing malodor mixture, is first experimentally established, such that, for a given concentration of each individual material of Group (I) or of Group (II), a precise MOC reduction effect can be established.

As used herein, "a malodor counteracting (MOC) composition" is to be understood as a mixture of ingredients as defined above and which is capable of reducing the perception of malodor, i.e. of an odor that is unpleasant or offensive to the human nose.

According to the invention, the individual MOC materials, and their mixtures, are shown to reduce the malodor perceived from compositions formed either according to International standards or as indicated in the examples further on, and which are representative of the various odors of interest generally recognized as being unpleasant or offensive to the human nose.

The amount of compound or compounds of Group (I) and of compound or compounds of Group (II) in the MOC composition of the invention can vary in a wide range of values comprised between 1 and 99% by weight of each of the two components, relative to the weight of the MOC composition. For each combination, the optimum relative concentrations can easily be established as indicated in the examples presented further on.

To provide the desired MOC effects to counteract malodor in the air surrounding a user of the MOC composition, or surrounding a surface to which one applies said composition, the latter may be used on its own or combined with other ingredients.

According to particular embodiments, the invention also concerns the use of the MOC compositions for preparing perfuming compositions containing other ingredients added mainly for their perfuming effect, such that the perfuming compositions of the invention comprise at least two distinct components, the MOC composition of the invention and a mixture of fragrance ingredients of a different nature.

To prepare a perfuming composition according to the invention, the MOC compositions may be admixed with perfuming ingredients of a different nature, the latter providing a desired hedonic effect of a pleasant nature. The MOC composition will typically constitute from 0.1 to 50% by weight, preferably from 5 to 50% by weight and more preferably from 9 to 20%, of the total weight of the perfuming composition according to the invention. The perfuming composition may also comprise solvents and adjuvants of current use in perfumery.

Likewise, the consumer products containing the MOC compositions of the invention, such as deodorants, air fresheners, products for the treatment of substrates such as textiles, kitchen and toilet surfaces, are also an object of the present invention.

According to another embodiment of the invention, there is provided a method to mask or cover malodors of the above-mentioned types, which method comprises applying to spaces, in particular air in closed spaces such as rooms and cupboards, or to any surface intended to be deodorized or freshened, a MOC composition according to the invention, in an amount sufficient to reduce, mask, eliminate or prevent any malodor perception from said surface or closed space. As examples of surfaces the odor of which can thus be improved, one can cite human skin and hair, animal skin or fur, kitchen and toilet surfaces, the surface of animal cages or litter containers, rubbish containers surfaces, textile and laundry surfaces, glass windows, dishes and crockery surfaces, etc.

Said perfuming co-ingredients are typically not compounds of Group (I) or of Group (II). Moreover, by "perfuming co-ingredient" it is meant here a compound which is used in perfuming a preparation or composition to impart a hedonic effect. In other words such a co-ingredient, must be recognized by a person skilled in the art as being able to impart or modify in a positive or pleasant way the odor of a composition, and not just as having an odor.

The nature and type of the perfuming co-ingredients of the MOC composition in the perfumes and perfuming compositions of the invention do not warrant a more detailed description here, which in any case would not be exhaustive, the skilled person being able to select them on the basis of its general knowledge and according to intended use or application and the desired perfuming effect. In general terms, these perfuming co-ingredients belong to chemical classes as varied as alcohols, aldehydes, ketones, esters, ethers, acetates, nitriles, terpene hydrocarbons, nitrogenous or sulfurous heterocyclic compounds and essential oils, and said perfuming co-ingredients can be of natural or synthetic origin. Many of these co-ingredients are in any case listed in reference texts such as the book by S. Arctander, Perfume and Flavor Chemicals, 1969, Montclair, N.J., USA, or its more recent versions, or in other works of a similar nature, as well as in the abundant patent literature in the field of perfumery. It is also understood that said co-ingredients may also be compounds known to release in a controlled manner various types of perfuming compounds.

As liquid carrier for such perfuming ingredients one may cite, as non-limiting examples, an emulsifying system, i.e. a solvent and a surfactant system, or a solvent commonly used in perfumery. A detailed description of the nature and type of solvents commonly used in perfumery cannot be exhaustive. However, one can cite as non-limiting example solvents such as di-propylene glycol, diethyl phthalate, isopropyl myristate, benzyl benzoate, 2-(2-ethoxyethoxy)-1-ethanol or ethyl citrate, which are the most commonly used.

The perfuming ingredients may also be present in a solid form, encapsulate or dispersed in solid carriers. As appropriate solid carriers one may cite, as non-limiting examples, absorbing gums or polymers, or yet encapsulating materials.

Examples of such materials may comprise wall-forming and plasticizing materials, such as mono, di- or tri-saccharides, natural or modified starches, hydrocolloids, cellulose derivatives, polyvinyl acetates, polyvinylalcohols, proteins or pectins, or yet the materials cited in reference texts such as H. Scherz, Hydrokolloids: Stabilisatoren, Dickungs- and Gehermittel in Lebensmittel, Band 2 der Schriftenreihe Lebensmittelchemie, Lebensmittelqualität, Behr's Verlag-GmbH & Co., Hamburg, 1996. The encapsulation is a well known process to a person skilled in the art, and may be performed, for instance, using techniques such as spray-drying, agglomeration or yet extrusion; or consists of a coating encapsulation method, including coacervation and complex coacervation techniques.

Furthermore, the invention's MOC compositions on their own or as components of the perfuming compositions according to the invention, can also be advantageously used in all the fields of modern perfumery to positively impart or modify the odor of a consumer product into which they are incorporated. Consequently, a consumer article or product comprising the MOC or perfuming compositions according to the invention, as defined above, is another object of the present invention.

Such consumer products typically comprise a consumer product base, in addition to the MOC and/or perfuming composition of the invention.

For the sake of clarity, by "consumer product base" we mean here a base which is distinct from, but compatible with, the MOC and perfuming compositions of the invention, and which is typically formed of substances capable of achieving the functional effect typically required from that product, such as cleaning, softening, freshening, deodorizing and others. Typical consumer product bases are the functional mixtures of ingredients that form the base of for example a surface or textile detergent or soap, a surface or textile softener, an air freshener, a cosmetic preparation, a deodorant, etc.

The nature and type of the constituents of the consumer product base do not warrant a more detailed description here, which in any case would not be exhaustive, the skilled person being able to select them on the basis of its general knowledge and according to the nature and the desired effect of said product.

Examples of suitable consumer product bases include those of solid or liquid detergents and fabric softeners as well as all the other articles common in perfumery, namely perfumes, colognes or after-shave lotions, perfumed soaps, shower or bath salts, mousses, oils or gels, hygiene products or hair care products such as shampoos, body-care products, deodorants or antiperspirants, air fresheners and also cosmetic preparations. Detergents include cleaning products for washing up or for cleaning various surfaces, e.g. intended for textile, dish or hard-surface treatment, whether they are intended for domestic or industrial use. Other perfumed articles are fabric refreshers, ironing waters, paper or non-woven substrates generally used for domestic cleaning of kitchen and bathroom surfaces in particular, or yet wipes and bleaches.

Some of the above-mentioned consumer product bases may represent an aggressive media for the MOC or perfuming compositions of the invention, so that it may be necessary to protect the latter from premature decomposition, for example by encapsulation.

The proportions in which the MOC compositions, or the perfuming compositions containing them, can be incorporated into the various aforementioned consumer articles or products may vary within a wide range of values. These values are dependent on the nature of the product as well as on the desired malodor counteracting effect that one wants to achieve. In many of these consumer products, the amount of perfuming composition containing the MOC component that is added to the consumer product is the typical amount that can be found currently in each type of consumer product and can be easily adjusted by the skilled formulator according to the perfuming and malodor counteracting effect that is desired to achieve and the nature of the consumer product in question.

In the case of air fresheners for instance, the air freshener composition intended for diffusion into its surroundings and which is usually contained in a recipient forming the main body of the air freshener, may be entirely formed of the perfuming compositions of the invention, together with an appropriate solvent such as water and or an organic solvent or may even consist of just the MOC composition according to the invention, if this is desired.

The malodor counteracting compositions and perfumes intended for air freshener use may also contain some optional ingredients acting as, for example, solvents, thickeners, anti-oxidants, dyes, bittering agents and uv inhibitors.

The presence of one or more solvents may be useful to have a single-phase liquid and/or to modulate the speed of evaporation of the active material into the surrounding air. Said solvents may belong to the families of isoparaffins, paraffins, hydrocarbons, namely glycols, glycol ethers, glycol ether esters, esters or ketones.

Examples of commercially available solvents useful to the invention are known under the tradename Isopar® H, J, K, L, M, P or V (isoparaffins; origin: Exxon Chemical), Norpar® 12 or 15 (paraffins; origin: Exxon Chemical), Exxsol® D 155/170, D 40, D 180/200, D 220/230, D 60, D 70, D 80, D 100, D 110 or D 120 (dearomatised Hydrocarbons; origin: Exxon Chemical), Dowanol® PM, DPM, TPM, PnB, DPnB, TPnB, PnP or DPnP (glycol ethers; origin: Dow Chemical Company), Eastman® EP, EB, EEH, DM, DE, DP or DB (glycol ethers; origin: Eastman Chemical Company), Dowanol® PMA or PGDA (glycol ether esters; origin: Dow Chemical Company) or Eastman® EB acetate, Eastman® DE acetate, Eastman® DB acetate, Eastman® EEP (all glycol ether esters; all origin: Eastman Chemical Company).

Other examples of solvents useful are dipropylene glycol, propylene glycol, ethylene glycol ethyl ether acetate, ethylene glycol diacetate, isopropyl myristate, diethyl phthalate, 2-ethylhexyl acetate, methyl n-amyl ketone or di-isobutyl ketone.

Dyes are other optional ingredients of the MOC compositions for airfresheners. Suitable dyes are oil-soluble and can be found in the Colour Index International, published by The Society of Dyers and Colourist. Non-limiting examples of suitable dyes are derivatives of the anthraquinone, methine, azo, triarylmethane, triphenylmethane, azine, aminoketone, spirooxazine, thioxanthene, phthalocyanine, perylene, benzopyran or perinone families. Examples of such dyes which are commercially available are known under the tradename Sandoplast® Violet RSB, Violet FBL, Green GSB, Blue 2B or Savinyl® Blue RS (all anthraquinone derivatives; origin: Clariant Huningue S.A.), Oilsol® Blue DB (anthraquinone; origin: Morton International Ltd.), Sandoplast® Yellow 3G (methine; origin: Clariant Huningue S.A.), Savinyl® Scarlet RLS (azo metal complex; origin: Clariant Huningue S.A.), Oilsol® Yellow SEG (monoazo; origin: Morton International Ltd.), Fat Orange® R (monoazo; origin: Hoechst AG), Fat Red® 5B (diazo;

origin: Hoechst AG), Neozapon® Blue 807 (phtalocyanine; origin: BASF AG), Fluorol® Green Golden (perylene; origin: BASF AG).

DESCRIPTION OF THE DRAWINGS

FIG. 1A to D show the % malodor reduction effectiveness of the MOC compositions A to D of the invention, described in Examples 1 to 4, against bathroom malodors.

FIG. 2A to D show the % malodor reduction effectiveness of the MOC compositions E to H of the invention, described in Examples 5 to 8, against tobacco malodor.

FIGS. 3A and B show the % malodor reduction effectiveness of the MOC compositions I and J of the invention, described in Examples 9 and 10, against kitchen malodor.

SPECIFIC EMBODIMENTS OF THE INVENTION

Figure 4:
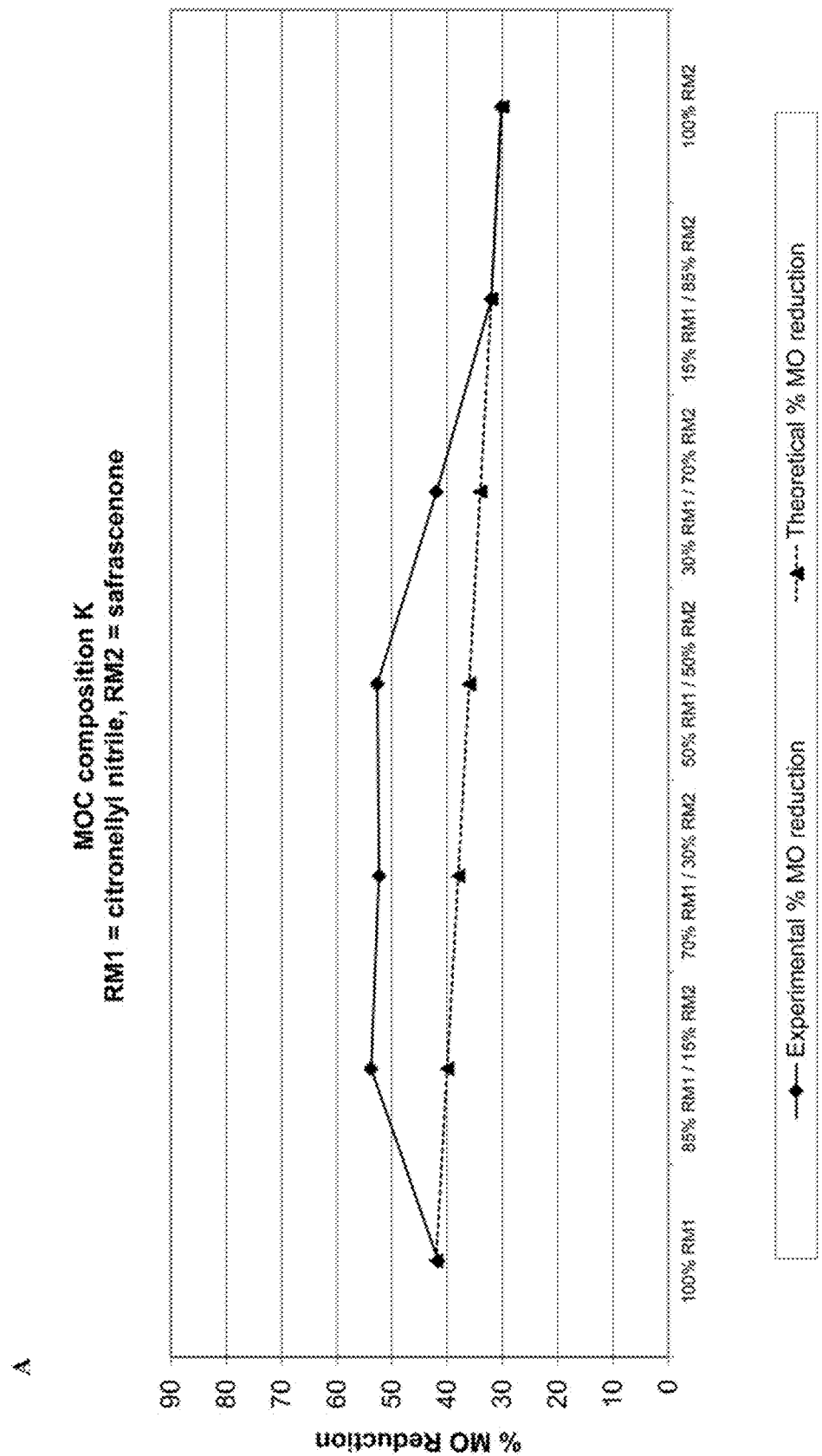
FIG. 4A to C compares the experimental and the theoretical % malodor reduction of bathroom malodor achieved by different MOC compositions comprising diverse proportions of each of the two components of three different pairs of compounds from Groups 1 and 2.
Figure 4:
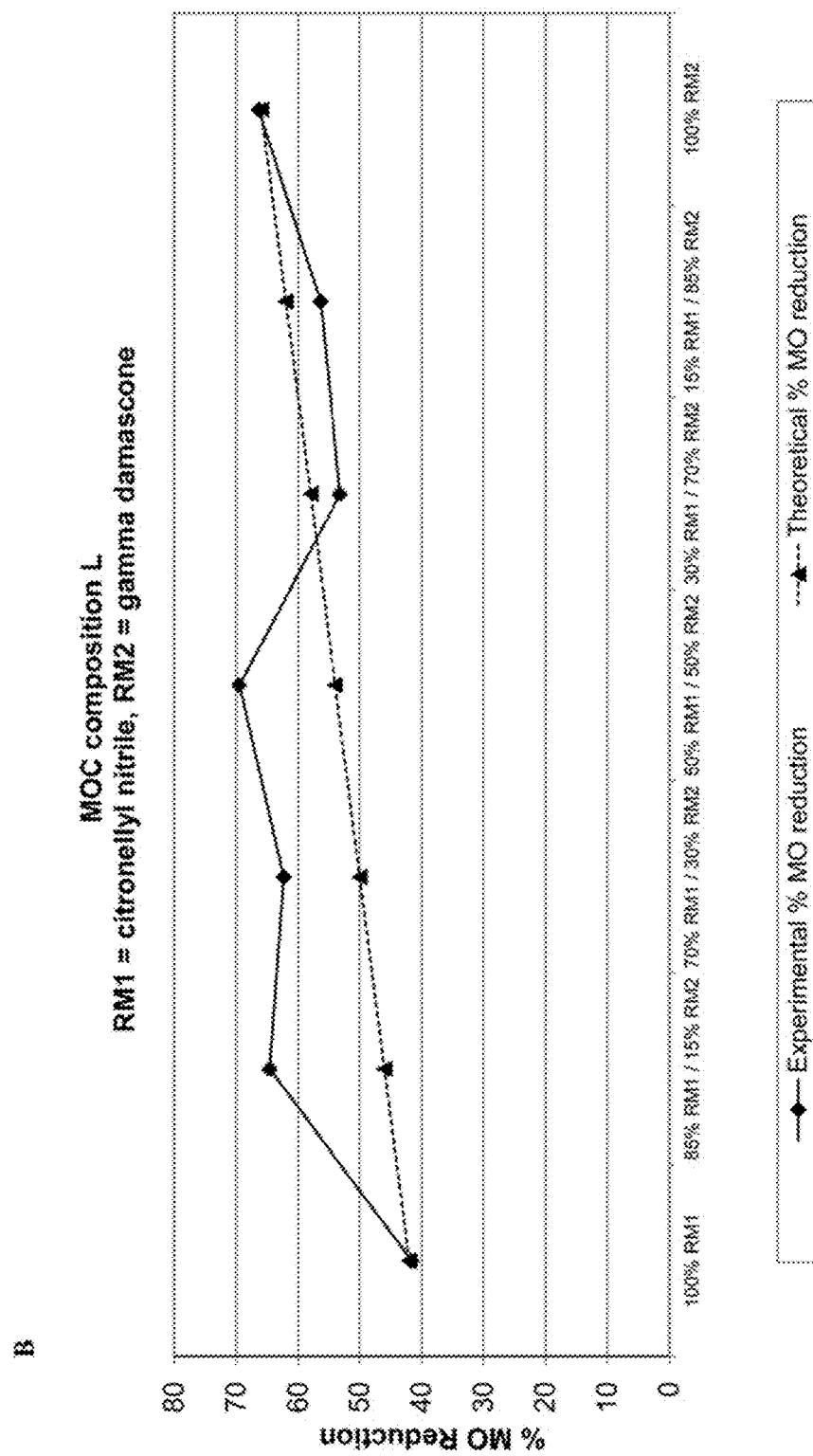
Figure 4:
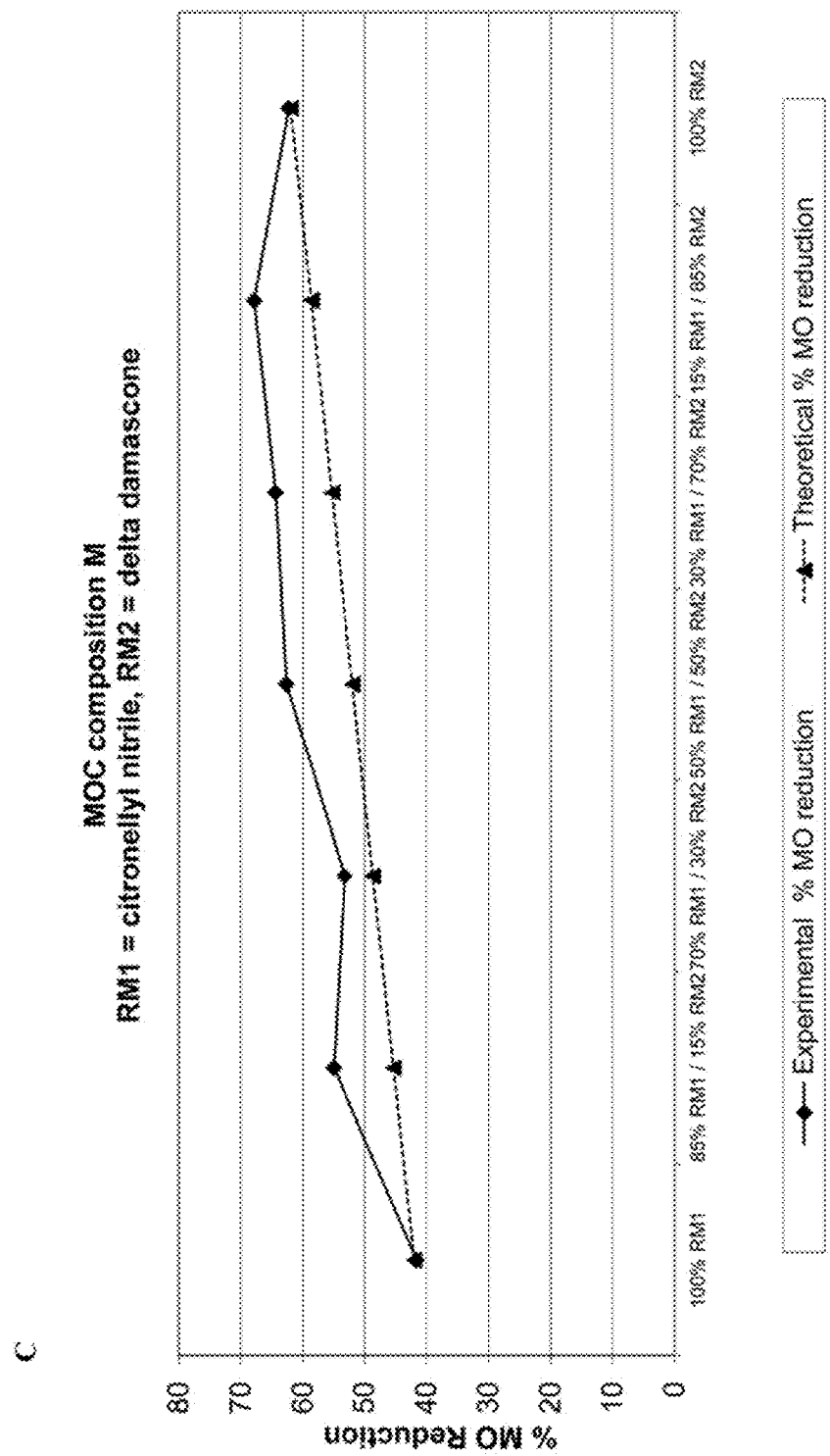

The invention will now be described in further detail by way of the following Examples.

Examples 1 to 10

Malodor Counteracting (MOC) Compositions and their Use to Reduce Perception of Malodor
A. Malodor Counteracting Effect of Individual Raw Materials—General Conditions of Evaluation A variety of raw materials from Groups (I) and (II) according to the invention were tested, using current sensory analysis methods, for their ability to reduce the perception of malodor of the bathroom, tobacco or kitchen type.
i) Malodor Compositions The typical malodor compositions used in these evaluations were composed of the materials indicated hereafter:

| Bathroom malodor* | |
|---|---|
| Ingredient | % w/w |
| Dipropylene glycol | 62.82 |
| Thioglycolic acid | 21.18 |
| n-Caproic acid | 6.00 |

| Bathroom malodor* | |
|---|---|
| Ingredient | % w/w |
| n-Methylmorpholine | 6.00 |
| 4-Methylphenyl 3-methylbutanoate | 2.18 |
| Skatole | 0.91 |
| 2-Naphthalenethiol | 0.91 |
| Total | 100.00 |

*U.S. General Services Administration Federal Supply Service Interim Specification, FA 200-5

Tobacco Malodor**

The tobacco malodor was prepared by extraction of cigarette's ash and smoked stub.

The ash and smoked stub of each cigarette was collected in a glass jar. For each cigarette smoked, 10 ml of ethanol were added. The mixture was stirred in a turbula mixer for 8 hours and then filtered. The filtrate was used as the tobacco malodor.

** origin: Firmenich SA, Geneva, Switzerland

| Kitchen malodor* | |
|---|---|
| Ingredient | % w/w |
| Diacetyl | 3.85 |
| Pyridine | 3.85 |
| Allyl sulfide | 9.23 |
| Methyl sulfide | 40.00 |
| Heptaldehyde | 3.85 |
| Paraldehyde | 1.90 |
| Propionic acid | 36.92 |
| Acetic acid, glacial | 0.40 |
| Total | 100.00 |

*U.S. General Services Administration Federal Supply Service Interim Specification, FA 200-3

In the following description, the test concentration of the specific malodor sample used in each case was always selected so as to provide a perceived malodor intensity, when evaluated in Sniffin® Pens as described below, that was approximately of the order of 4 to 5 units in the scale described under (ii) below.

The three types of malodor samples that were perceived as having about 4.5 malodor intensity were are as follows:
Bathroom malodor—1% in propylene glycol
Tobacco malodor—30% in propylene glycol
Kitchen malodor—0.3% in propylene glycol.
ii) Sample Preparation Each raw material to be evaluated for MOC effect against one of the malodor compositions was diluted at 10% by weight in propylene glycol. The typical bathroom malodor sample was diluted at 2% by weight in propylene glycol, the tobacco malodor was diluted at 60% by weight in propylene glycol and the kitchen malodor was diluted at 0.6% by weight in propylene glycol.

3 G of each raw material solution as above and 3 g of the bathroom, tobacco or kitchen malodor solution, were then mixed together in a separate beaker. Once fully homogenized, 4 g of the resulting raw material/malodor solution were applied to a Sniffin Pen (Sniffin® Pens are commercially available from Heinrich Burghart GmbH). The Sniffin Pens thus obtained were left to equilibrate before the sensory evaluation test.

iii) MOC Effect Against Bathroom Malodor

Each sensory test comprised the following samples:

2 Blind negative controls with bathroom malodor only @ 1%

Blind positive control with a given MOC raw material @ 5%

4 Blind test samples with 5% of a given test raw material and 1% of bathroom malodor.

The samples were evaluated by a panel of at least 20 trained panelists. By "trained panelists" we mean here individuals that had previously been screened for olfactive acuity and were experienced in rating the perfume intensity of air freshener products. Moreover, the panelists were prior acquainted with the malodor sample before carrying out the evaluations of the raw material samples counteracting effect.

The samples were presented to the panelists in Sniffin Pens. Each Sniffin Pen was labeled with a randomly generated 3 digit code. Sniffin Pens were presented to the panelist according to a Latin square design order. These are presentation methods in which the samples are presented in a balanced manner, each product being presented the same number of times in every position, and every possible pair is represented the same number of times (see Multivariate analysis of data in sensory science, edited by T. Næs, E. Risvik, Norwegian Food Research Institute, Oslovein, Norway, 1996, Elsevier, E. A. Hunter, Chapter 2).

After smelling the malodor reference sample first to familiarize themselves with the malodor, the panelists were asked to rate the malodor intensity and the total odor intensity of each sample, based on a linear 1-7 scale (1=no odor-7=extremely strong odor) as shown here below:

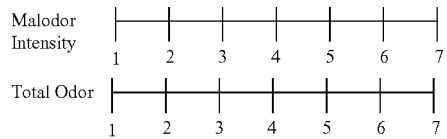

The data generated from the panel's evaluations was statistically analyzed in each case using variance analysis (ANOVA, $\alpha=0.05$) and least significance difference (LSD, $\alpha=0.05$).

A typical example of the results is shown in Table 1 for bathroom malodor counteracting effect of four generic test raw materials (RM).

TABLE 1

Bathroom malodor counteracting by raw materials RM 1-4

| Sample No. | Sample Description (w/w % of ingredients relative to total sample weight) | Malodor Intensity | Overall Odor Intensity |
|---|---|---|---|
| 1 | RM 1 (5%) + Bathroom Malodor FA 200-5 (1%) | $x_1$ | $y_1$ |
| 2 | RM 2(5%) + Bathroom Malodor FA 200-5 (1%) | $x_2$ | $y_2$ |
| 3 | RM 3(5%) + Bathroom Malodor FA 200-5 (1%) | $x_3$ | $y_3$ |
| 4 | RM 4(5%) + Bathroom Malodor FA 200-5 (1%) | $x_4$ | $y_4$ |
| 5 | Bathroom Malodor FA 200-5 (1%) | $x_5$ | $y_5$ |
| 6 | Bathroom Malodor FA 200-5 (1%) | $x_6$ | $y_6$ |
| 7 | RM* (5%) | $x_7$ | $y_7$ |

*Raw material n, n being an integer from 1 to 4

The results of the evaluation of the malodor samples 5 and 6 allow the calculation of a malodor total odor mean value using the equation:

$$x_{mal}=(x_5+x_6)/2.$$

This $x_{mal}$ value is then used to calculate the % of malodor reduction, or malodor counterancy effect MOC, of each individual raw material RM 1 to 4, according to the following equation:

$$\text{MO reduction}_n=100*(1-(x_n-1)/(x_{mal}-1))$$

n being an integer of 1 to 4, designating the specific raw material in question in each evaluation test.

The above example is typical for all MOC evaluation tests carried out with individual malodor counteracting raw materials against the three types of malodor samples, bathroom, tobacco and kitchen malodors.

B. Malodor Counteracting Effect of the MOC Compositions According to the Invention—General Conditions of Evaluation i) Sample Preparation Each of the two raw materials to be admixed to provide a MOC composition according to the invention was diluted at 10% by weight in propylene glycol. The typical bathroom malodor sample was diluted at 2% by weight in propylene glycol, the tobacco malodor was diluted at 60% by weight in propylene glycol and the kitchen malodor was diluted at 0.6% by weight in propylene glycol.

1.5 G of each of the two raw material solutions obtained were admixed to provide the MOC composition solution which was added to 3 g of the bathroom, tobacco or kitchen malodor solution in a separate beaker. Once fully homogenized, 4 g of the resulting MOC composition solution/malodor solution were applied to a Sniffin Pen (Sniffin Pens are commercially available from Heinrich Burghart GmbH). The Sniffin Pens thus obtained were left to equilibrate before the sensory evaluation test.

ii) Effect of the MOC Compositions Against Malodor

The samples as prepared above were evaluated in a manner similar to that described under A., using the same methods, for malodor counteracting effect against the same typical malodor samples. The results of the evaluations for a specific MOC composition thus provide a generic Table 2, as follows, for each MOC composition.

TABLE 2

Bathroom malodor counteracting by MOC compositions

| Sample No. | Sample Description (w/w % of ingredients relative to total sample weight) | Malodor Intensity | Overall Odor Intensity |
|---|---|---|---|
| 8 | MOC Composition 1 (5%) + Bathroom Malodor FA 200-5 (1%) | $X_8$ | $Y_8$ |
| 9 | MOC Composition 2 (5%) + Bathroom Malodor FA 200-5 (1%) | $X_9$ | $Y_9$ |
| 10 | MOC Composition 3 (5%) + Bathroom Malodor FA 200-5 (1%) | $X_{10}$ | $Y_{10}$ |
| 11 | MOC Composition 4 (5%) + Bathroom Malodor FA 200-5 (1%) | $X_{11}$ | $Y_{11}$ |
| 12 | Bathroom Malodor FA 200-5 (1%) | $X_{12}$ | $Y_{12}$ |
| 13 | Bathroom Malodor FA 200-5 (1%) | $X_{13}$ | $Y_{13}$ |
| 14 | MOC composition*(5%) | $X_{14}$ | $Y_{14}$ |

*MOC composition n, n being an integer from 8 to 11

The results of the evaluation of the malodor samples 12 and 13 allow the calculation of a malodor total odor mean value using the equation:

$$x_{mal}=(x_{12}+x_{13})/2.$$

This $x_{mal}$ value is then used to calculate the % of malodor reduction of each MOC composition, according to the following equation:

$$\% \text{ MO reduction}_n=100*(1-(x_n-1)/(x_{mal}-1))$$

n being an integer of 8 to 11, designating the specific MOC composition in question in each evaluation test.

A theoretical % malodor reduction value for each MOC composition, against each malodor type, is also calculated as the arithmetic average of the % malodor reduction values obtained as in A. for the two raw materials that are combined in each MOC composition of the invention.

For example, if MOC composition 1 in Table 2 is a 50:50 mixture of raw materials RM 1 and RM 2 of Table 1, then the theoretical % malodor reduction value for MOC composition 1 against bathroom malodor is equal to $(x_1+x_2)/2$, $x_1$ and $x_2$ being the same values as in Table 1. If this theoretical value is below the experimental Table 2 $X_8$ value obtained with this MOC composition 1 against bathroom malodor, then the combination of raw materials RM 1 and RM 2 provides an unexpected synergic effect against bathroom malodor.

The above example is typical for all MOC compositions evaluation tests carried out against the three types of malodor samples, bathroom, tobacco and kitchen malodors.

C. MOC Compositions According to the Invention and their Use to Counteract Malodor i) Effect Against Bathroom Malodor—Examples 1 to 4

A variety of MOC compositions A to D were prepared by admixing the corresponding raw materials indicated in Table 3, in a range of relative proportions varying from 1:99 to 99:1 of each of the raw materials indicated.

TABLE 3

MOC compositions and their components

| MOC Composition | Raw Material A* | Raw Material B* |
|---|---|---|
| A | Nitrile described in U.S. Pat. No. 6,180,814 | Violette BC[1] |
| B | Citronellyl nitrile | Koumalactone[2] |
| C | Citronellyl nitrile | γ-Methylionone |
| D | 2-Propyl-1-heptanenitrile | α-Damascone |

[1]β-Ionone
[2]perhydro-3,6-dimethyl-benzo[b]furan-2-one

FIG. 1A to D show the % malodor reduction effectiveness of the MOC compositions A to D against bathroom malodors.

ii) Effect Against Tobacco Malodor—Examples 5 to 8

A variety of MOC compositions E to H were prepared by admixing the corresponding raw materials indicated in Table 4, in a range of relative proportions varying from 1:99 to 99:1 of each of the raw materials indicated.

TABLE 4

MOC compositions and their components

| MOC Composition | Raw Material A* | Raw Material B* |
|---|---|---|
| E | Citronellyl Nitrile | 1-(4,66-trimethyl-1,3-cyclohexadien-1-yl)-2-buten-1-one |
| F | Citronellyl Nitrile | 1-(2,66-trimethyl-1(2)-cyclohexen-1-yl)-1,6-heptadien-3-one |
| G | Citronellyl Nitrile | δ-Damascone |
| H | Citronellyl Nitrile | γ-Methylionone |

*Origin: Firmenich SA, Geneva, Switzerland

FIG. 2A to D show the % malodor reduction effectiveness of the MOC compositions E to H against tobacco malodor.

iii) Effect Against Kitchen Malodor—Examples 9 and 10

MOC compositions I and J were prepared by admixing the corresponding raw materials indicated in Table 5, in a range of relative proportions varying from 1:99 to 99:1 of each of the raw materials indicated.

TABLE 5

MOC compositions and their components

| MOC Composition | Raw Material A* | Raw Material B* |
|---|---|---|
| I | Citronellyl Nitrile | δ-Damascone |
| J | Citronellyl Nitrile | γ-Methylionone |

*Origin: Firmenich SA, Geneva, Switzerland

FIGS. 3A and B show the % malodor reduction effectiveness of the MOC compositions I and J against kitchen malodor.

The results presented in FIGS. 1, 2 and 3 clearly show that the MOC compositions of the invention are surprisingly effective at counteracting bathroom, tobacco and kitchen malodor, all the compositions A to J having consistently performed above the theoretical effect that one might have expected if each pair had the effects simply added up once the materials were combined.

Moreover, a very large sample of other pairs of perfumery raw materials were tested without such a result being observed. In fact in many cases, a negative influence could be seen when two such materials were combined in a similar manner as exemplified above. This was especially the case when two perfumery raw materials carrying a lateral $R^1$ substituent group in the formula (I) type compounds derived from a carboxylic acid, such as a ketone or aldehyde group, were admixed amongst themselves.

Example 11

The ability of the preferred MOC compositions K to M from Table 6 below to mask the synthetic bathroom malodor exposed above has been tested with the compounds of Groups 1 and 2 mixed in different proportions.

TABLE 6

MOC compositions and their components

| MOC Composition | Raw Material A* | Raw Material B* |
|---|---|---|
| K | Citronellyl nitrile | Safrascenone[1)] |
| L | Citronellyl nitrile | γ-Damascone |
| M | Citronellyl nitrile | α-Damascone |

*Origin: Firmenich SA, Geneva, Switzerland
[1)](E)-1-(4,6,6-trimethyl-1,3-cyclohexadien-1-yl)-2-buten-1-one As in Examples 1 to 10 above, the malodor reduction observed during the sensory tests is compared to the theoretical malodor reduction that can be expected for each different ratio. The results are shown in FIG. 4A to C. The theoretical curve (dotted line) is obtained by tracing a straight line between the values of malodor reduction obtained experimentally for each of the raw materials alone.

The samples have been prepared in the same way as for the previous examples, except for the respective amounts of the two MOC ingredients, as represented in the figure. The sensory and statistical analyses have also been performed as described above. These experimental results are summarized in the graphs of FIG. 4 (continuous line).

A synergy is observed when the percentage of malodor reduction of the experimental curve is higher than the theoretical percentage. The three graphs of FIG. 4 show that, for each pair of compounds from Groups (I) and (II), certain proportions are particularly effective to mask the bathroom malodor.

The compositions corresponding to the latter proportions are particularly advantageous and the invention therefore relates namely to the following preferred compositions:
a) a MOC composition of safrascenone and citronellyl nitrile, in relative proportions comprised between 1:99 and 70:30 w/w respectively;
b) a MOC composition of γ-damascone and citronellyl nitrile, in relative proportions comprised between 1:99 and 50:50 w/w respectively;
c) a MOC composition of δ-damascone and citronellyl nitrile, in relative proportions comprised between 1:99 and 99:1 w/w respectively.

Example 12

Malodor Counteracting (MOC) Compositions Comprising a Compound of Formula (I) as the Group (I) Component and their Use to Reduce Perception of Malodor A variety of MOC compositions according to the invention were prepared by admixing a given nitrile compound as the Group (II) component with a compound of formula (I) having a double bond in position alpha or beta relative to the functional substituent $R^1$.

Thus, the following compounds of formula (I) were admixed with the nitriles indicated in Table 7 here below, in a relative proportion of 50:50, to prepare six MOC compositions according to the invention that presented a particularly useful effectiveness against bathroom malodor.

TABLE 7

| Compound of formula (I)* | Nitrile* |
|---|---|
| α-Ionone | Nitrile described in U.S. Pat. No. 6,180,814 |
| β-Ionone | Nitrile described in U.S. Pat. No. 6,180,814 |
| α-Methylionone | Citronellyl nitrile |
| β-Methylionone | Citronellyl nitrile |

TABLE 7-continued

| Compound of formula (I)* | Nitrile* |
|---|---|
| α-Damascone | 2-Propyl-1-heptanitrile |
| β-Damascone | 2-Propyl-1-heptanitrile |

*Origin: Firmeinch SA, Geneva, Switzerland

Figure 5:
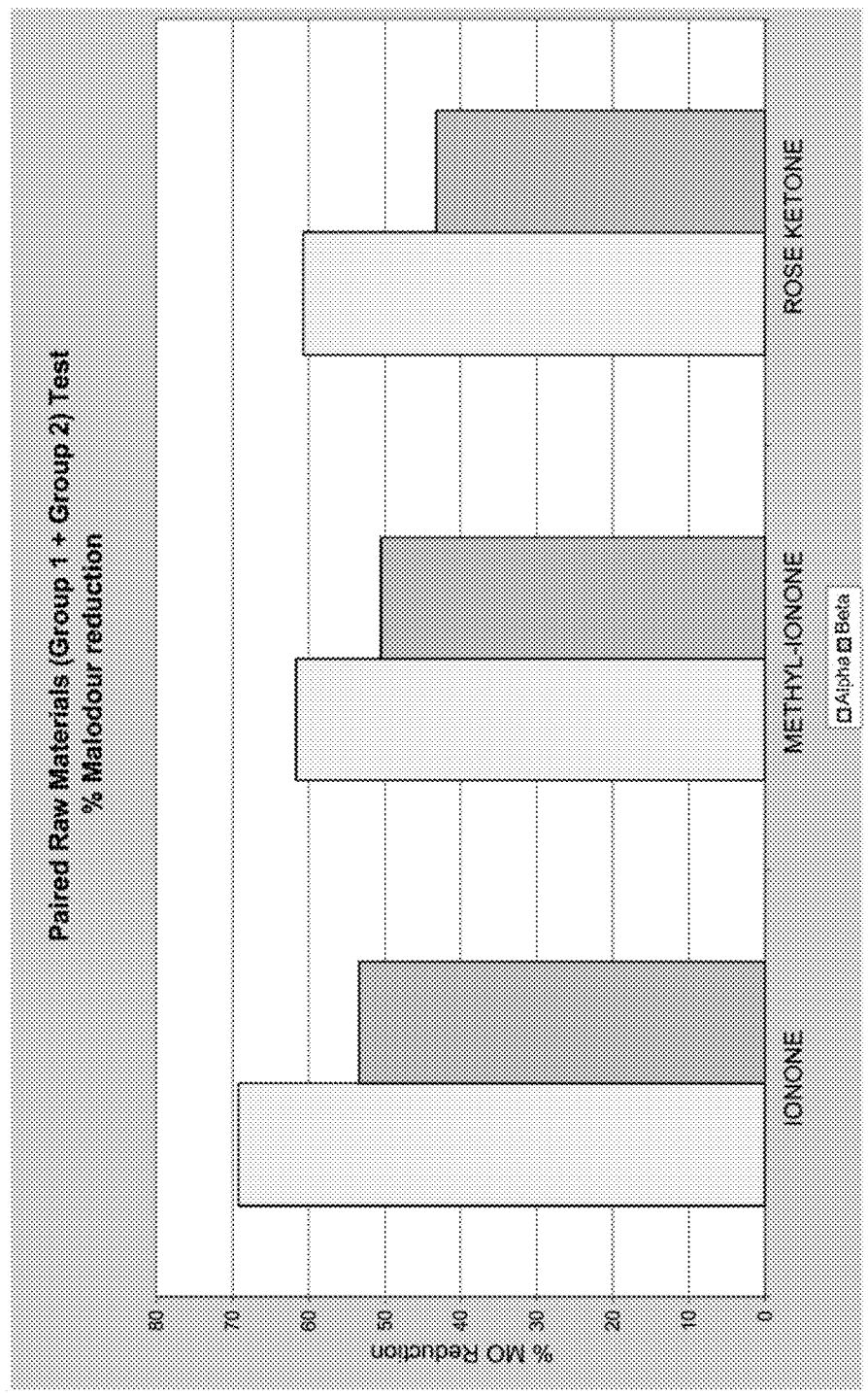
FIG. 5 summarizes the results of the evaluation of the six MOC compositions of the invention described in Example 12 against bathroom malodor and shows that the malodor counteracting activity of the MOC compositions comprising a compound (I) having a ring double bond in position alpha relative to the substituent group $R^1$ perform consistently better than those comprising a compound (I) wherein the double bond in the ring lies in position beta relative to $R^1$.

The methods used were identical to those described in the general method section of Examples 1 to 10. FIG. 5 summarizes the results of the evaluation of the six MOC compositions grouped by the type of structure of the compounds (I) and shows that the malodor counteracting activity of the MOC compositions comprising a compound (I) having a ring double bond in position alpha relative to the substituent $R^1$ performed consistently better than those comprising a compound (I) wherein the double bond in the ring is in position beta.

Figure 6:
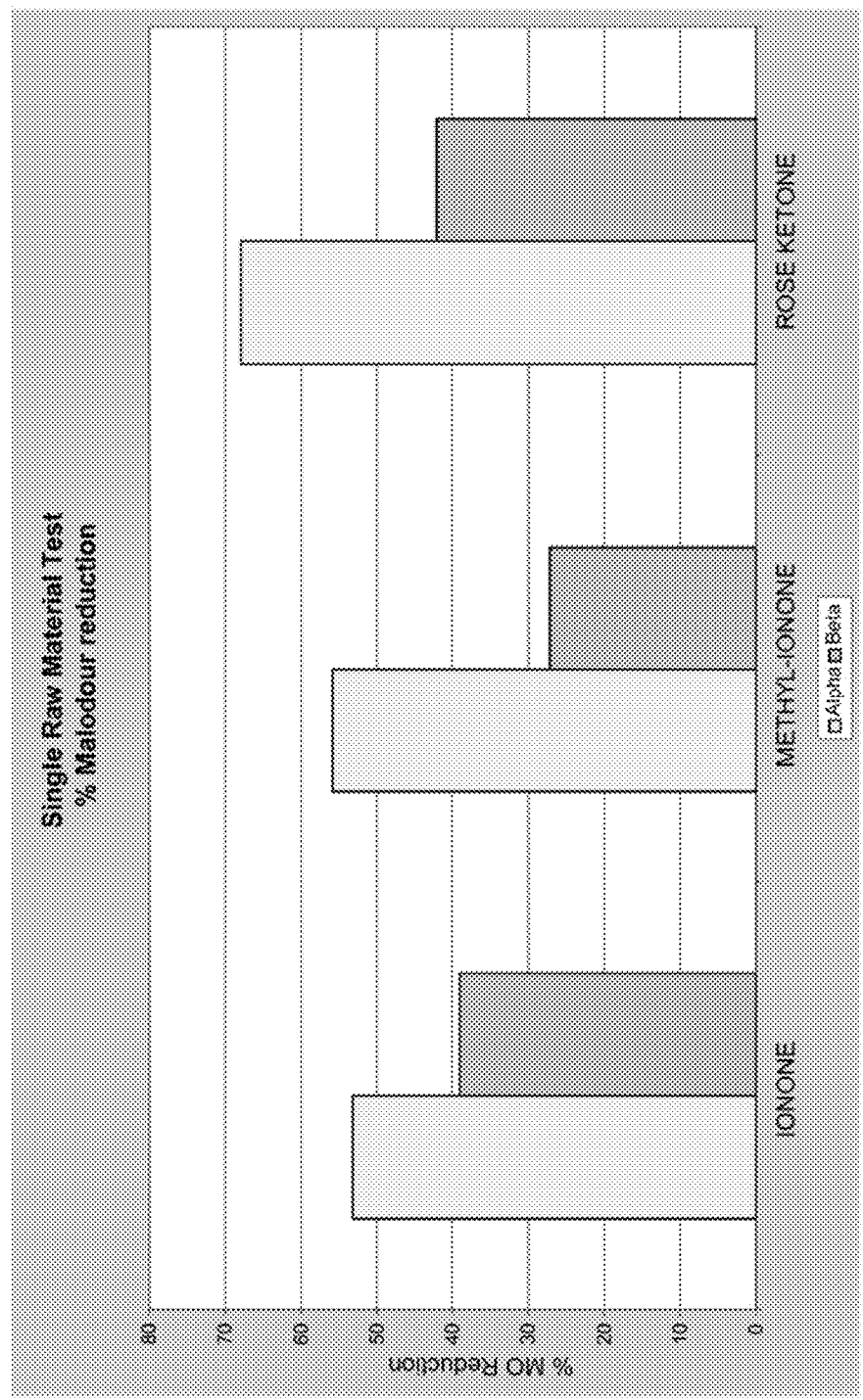
FIG. 6 represents the malodor counteracting activity of each Group (I) raw material compound of formula (I) used on its own against bathroom malodor, as described in Example 12.

When comparing with the results, represented in FIG. 6, obtained with each corresponding raw material compound (I) used on its own and tested in identical concentration against the bathroom malodor, most of the MOC compositions of the invention again showed an improved reduction of the perceived malodor, relative to the individual raw material of formula (I).

Example 13

Performance of a Perfuming Composition Comprising a MOC Composition of the Invention in Terms of Body Malodor Masking onto Washed Fabrics.

The ability of a perfuming composition according to the invention to mask body malodor, more specifically sweat malodor, was tested in a laundry product. Two different perfuming compositions, containing respectively 4.5% and 9.5% by weight of the MOC composition relative to the total weight of a same perfume were prepared. The formula of the MOC composition used is provided in Table 8 below. Each of the perfuming compositions above was added to a laundry product base in an amount of 0.4% by weigh, relative to the total weight of the laundry product, to prepare two laundry products according to the invention. The formula of the MOC composition used in the present example is provided in Table 8 below.

TABLE 8

Formula of the MOC composition

| Ingredient | Quantity |
|---|---|
| 4-undecanolide | 60.61 |
| Citronellyl nitrile | 3.03 |
| δ-damascone | 1.52 |
| 8-methyl-α-ionone + 10-mehyl-α-ionone | 22.72 |
| Neobutenone alpha | 3.03 |
| (E)-4-(2,6,6-trimethyl-1-cyclohexen-1-yl)-3-butene-2-one | 9.09 |
| Total | 100.00 |

Eighteen swatches of polyester Lycra® were washed together with a ballast so as to obtain a total wash load of 2.5 kg. The latter were washed in a front load European washing machine at 40° C., without pre-wash, using 4 rinse cycles and 100 g of liquid detergent. The washed load was then line-dried during 24 hours under controlled conditions (22° C.-60% relative humidity).

Different test samples were prepared by washing the swatches with the laundry product containing the perfuming composition comprising either 4.5% or 9.5% by weight of the MOC composition. The samples were washed, dried and then sprayed with 0.33 g of the sweat malodor composition, one hour before the sensory evaluation. One negative control was prepared by washing the swatch with the laundry product without any perfuming composition and by spraying it with the body malodor composition. Finally, two positive controls were prepared by washing swatches with the laundry products containing the perfuming composition either with 4.5% or with 9.5% by weight of the MOC composition, no body malodor composition being applied.

The sensory analysis was performed with a panel of trained panelists. They were asked to rate the overall odor intensity, the perfume intensity and the malodor intensity of each sample and control, on a linear 0-10 scale. The results of this sensory analysis were then analysed statistically. The final results are summarized in the charts of FIGS. 7A and B.

Figure 7:
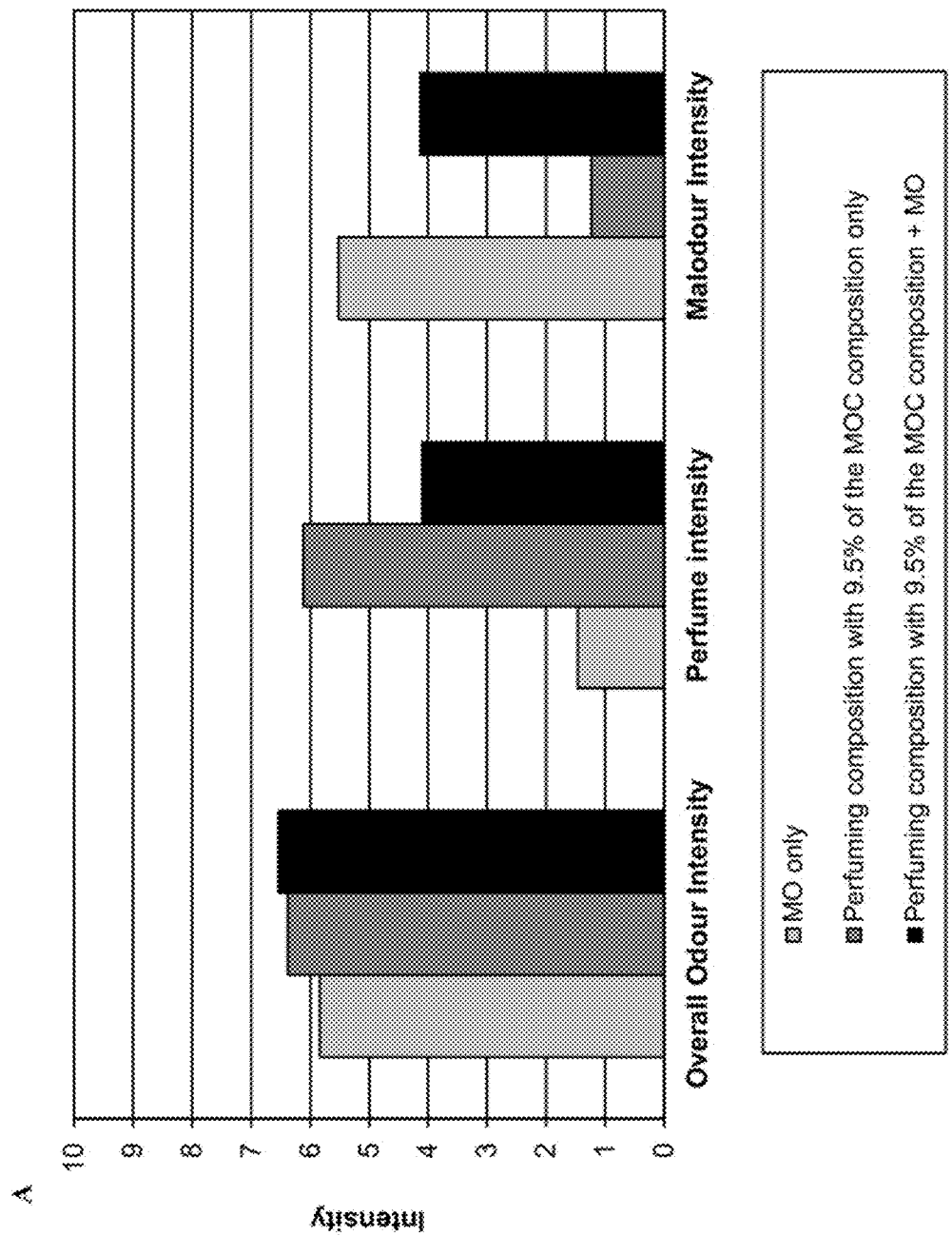
FIGS. 7A and B show the ability of a laundry product containing a perfuming composition comprising a MOC composition of the invention to reduce body malodor. The results are presented for two different concentrations of the MOC composition, i.e. 4.5% and 9.5% by weight, relative to the total weight of the perfuming composition.
Figure 7:
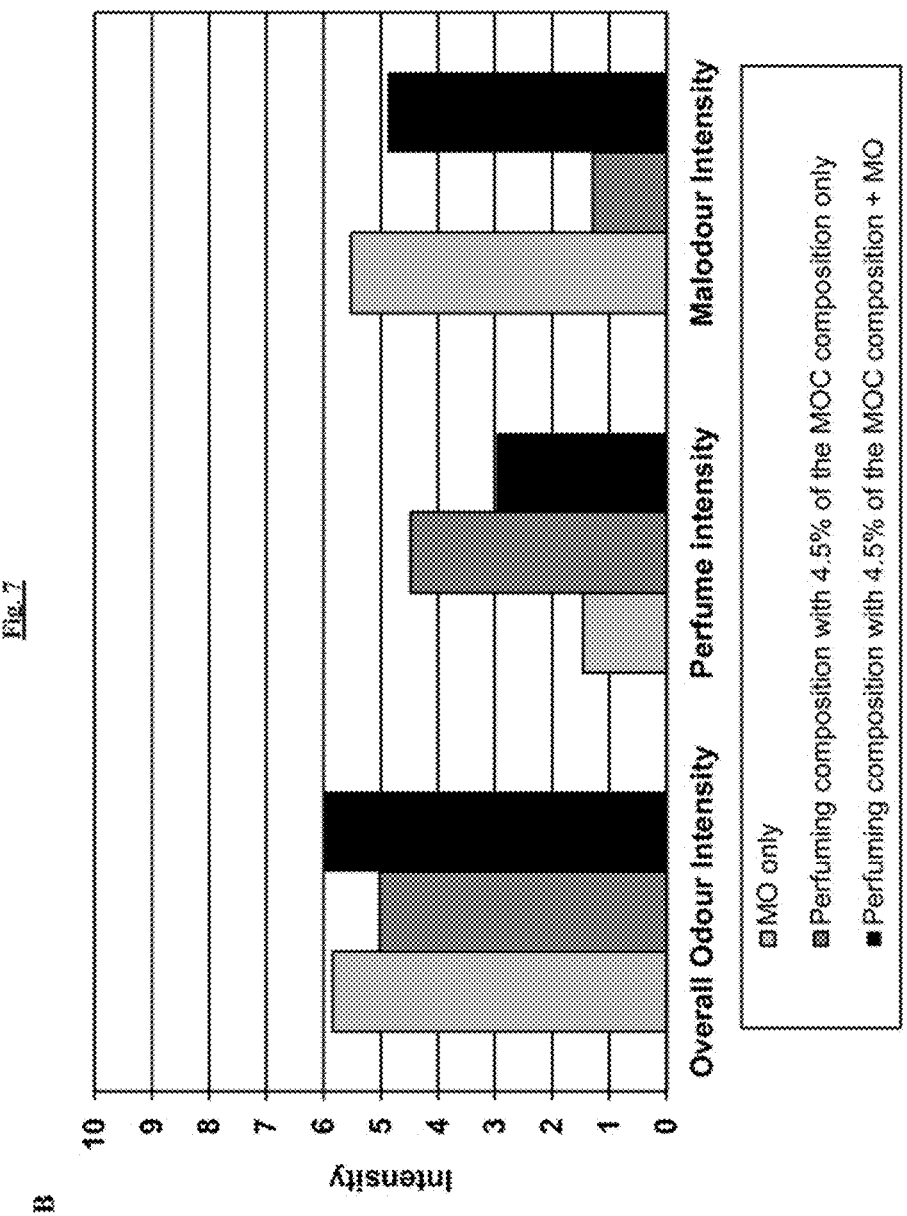

FIG. 7B shows that a slight malodor reduction is already observed with the perfuming composition comprising 4.5% by weight of the MOC composition. FIG. 7A shows that when the perfuming composition comprises a higher amount of the MOC composition of the invention (9.5% by weight), a significant reduction of the malodor is achieved.

According to the invention, there can be used any perfume composition to which the MOC mixtures are added to provide similar effects. In the present example, we used a perfume having a top note with green, apple, aldehydic and pine connotations, completed by violet, rose medium notes and a sandalwood, plum, musk character as the bottom note.

The invention claimed is:

1. A malodor counteracting (MOC) composition comprising:
    a. citronellyl nitrile; and
    b. a compound selected from the group consisting of (E)-1-(4,6,6-trimethyl-1,3-cyclohexadien-1-yl)-2-buten-1-one, γ-Damascone, and δ-Damascone,
    wherein the ratio of citronellyl nitrile to the γ-Damascone compound is between 85%:15% w/w and 50%:50% w/w, and
    wherein the ratio of the citronellyl nitrile to the δ-Damascone or the (E)-1-(4,6,6-trimethyl-1,3-cyclohexadien-1-yl)-2-buten-1-one compound is between 85%:15% w/w and 15%:85% w/w.

2. The composition of claim 1, wherein the MOC composition comprises citronellyl nitrile and (E)-1-(4,6,6-trimethyl-1,3-cyclohexadien-1-yl)-2-buten-1-one.

3. The composition of claim 1, wherein the MOC composition comprises citronellyl nitrile and γ-Damascone.

4. The composition of claim 1, wherein the MOC composition comprises citronellyl nitrile and δ-Damascone.

5. A consumer article or product comprising the MOC composition according to claim 1, together with a consumer product base.

6. The consumer article or product according to claim 5 wherein the article or product is selected from the group consisting of a solid detergent, a liquid detergent, a fabric softener, a bleach, a perfume, a cologne, an after-shave lotion, a perfumed soap, a shower or bath salt, mousse, oil, gel, a hygiene product, a hair product, a shampoo, a hairspray, a hair conditioner, a deodorant, an antiperspirant, an air freshener, a cosmetic preparation, a fabric refresher, an ironing water, a paper substrate, a non-woven substrate, and a wipe.

7. A perfuming composition comprising:
    a. between 0.1 to 50% by weight of a malodor counteracting (MOC) composition, comprising:
        i. citronellyl nitrile; and
        ii. a compound selected from the group consisting of (E)-1-(4,6,6-trimethyl-1,3-cyclohexadien-1-yl)-2-buten-1-one, γ-Damascone, and δ-Damascone,
        wherein the ratio of citronellyl nitrile to the γ-Damascone compound is between 85%:15% w/w and 50%:50% w/w and
        wherein the ratio of the citronellyl nitrile to the δ-Damascone or the (E)-1-(4,6,6-trimethyl-1,3-cyclohexadien-1-yl)-2-buten-1-one compound is between 85%:15% w/w and 15%:85% w/w; and
    b. a solvent or an adjuvant useful in perfumery.

8. The perfuming composition of claim 7, wherein the MOC composition constitutes 4.5 to 50% by weight of the perfuming composition.

9. The perfuming composition of claim 7, wherein the MOC composition comprises citronellyl nitrile and (E)-1-(4,6,6-trimethyl-1,3-cyclohexadien-1-yl)-2-buten-1-one.

10. The perfuming composition of claim 7, wherein the MOC composition comprises citronellyl nitrile and γ-Damascone.

11. The perfuming composition of claim 7, wherein the MOC composition comprises citronellyl nitrile and δ-Damascone.

12. A consumer article or product comprising the perfuming composition according to claim 7, together with a consumer product base.

13. The consumer article or product according to claim 12 wherein the article or product is selected from the group consisting of a solid detergent, a liquid detergent, a fabric softener, a bleach, a perfume, a cologne, an after-shave lotion, a perfumed soap, a shower or bath salt, mousse, oil, gel, a hygiene product, a hair product, a shampoo, a hairspray, a hair conditioner, a deodorant, an antiperspirant, an air freshener, a cosmetic preparation, a fabric refresher, an ironing water, a paper substrate, a non-woven substrate, and a wipe.

* * * * *